United States Patent
Sugimoto et al.

[11] Patent Number: 5,718,667
[45] Date of Patent: Feb. 17, 1998

[54] ORAL HYGIENE INSTRUMENT

[75] Inventors: Tomohisa Sugimoto, Higashiosaka; Tsuguo Matsui, Kyoto; Seiji Kita, Takatsuki, all of Japan

[73] Assignee: Sunstar Kabushikigaisha, Takatsuki, Japan

[21] Appl. No.: 545,765

[22] PCT Filed: May 24, 1994

[86] PCT No.: PCT/JP94/00825
§ 371 Date: Nov. 22, 1995
§ 102(e) Date: Nov. 22, 1995

[87] PCT Pub. No.: WO94/27466
PCT Pub. Date: Dec. 8, 1994

[30] Foreign Application Priority Data

| May 27, 1993 | [JP] | Japan | 5-028029 U |
| Nov. 30, 1993 | [JP] | Japan | 5/063975 U |

[51] Int. Cl.$^6$ ............................................. A61H 13/00
[52] U.S. Cl. .................................... 601/139; 132/322
[58] Field of Search .......................... 132/321, 322; 601/139, 141, 142; 15/22.1, 22.2

[56] References Cited

U.S. PATENT DOCUMENTS

| 3,466,689 | 9/1969 | Aurelio et al. | 601/142 |
| 3,588,936 | 6/1971 | Duve | 15/22.1 |
| 3,967,617 | 7/1976 | Krolik | 601/142 |
| 4,991,249 | 2/1991 | Suroff | 15/22.1 |

FOREIGN PATENT DOCUMENTS

| 1414679 | 9/1965 | France | 15/22.1 |
| 48-31723 | 9/1973 | Japan . | |
| 50-86491 | 7/1975 | Japan . | |
| 52-32463 | 3/1977 | Japan . | |
| 55-5454 | 1/1980 | Japan . | |
| 2-92722 | 7/1990 | Japan . | |
| 3-27723 | 3/1991 | Japan . | |

Primary Examiner—Nicholas D. Lucchesi
Attorney, Agent, or Firm—Armstrong, Westerman, Hattori, McLeland & Naughton

[57] ABSTRACT

An oral hygiene instrument according to this invention by means of vibration generating means vibrates by way of a holder member an oral hygiene tool removably attached to the holder member and comprises a cap member having a cap side thread portion which meshes with a holder side thread portion formed at a first end of the holder member which cap member is removably attached to the first end of the holder member and closes an opening in the first end of the holder member, a seal ring fitted on a portion of the holder member or the cap member at the external end of the part where the two members mesh which seal ring is pressed upon by either the cap member or the holder member and seals the gap between the holder member and the cap member within a range of a predetermined angle of screwing of the cap member with respect to the holder member from a late stage to completion of said screwing, and a holder side contact piece and a cap side contact piece mounted in the holder member and the cap member respectively which approach each other when the cap member is screwed with respect to the holder member and in the range of the predetermined angle make contact and close a circuit supplying electricity to the vibration generating means. In order to removably attach the oral hygiene tool to the holder member, a bottomed cylindrical holding part having a plurality of axially extending first slits and second slits is formed at a second end of the holder member, and the oral hygiene tool is provided with a shaft portion which can be inserted into the holding part.

11 Claims, 18 Drawing Sheets

[ Fig. 2 ]
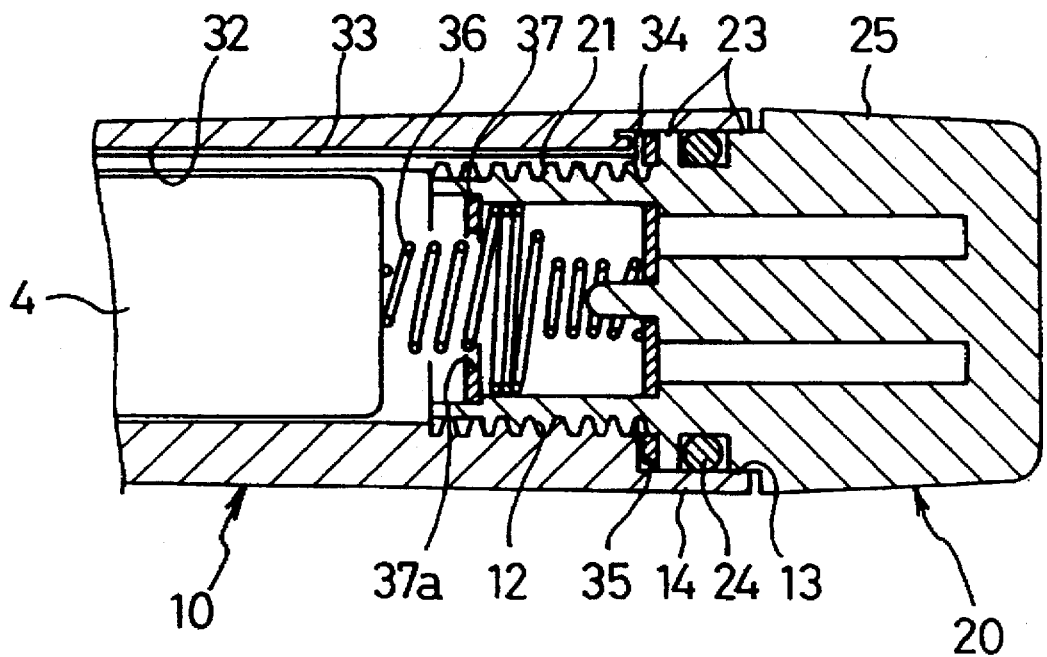

[ Fig. 3 ]
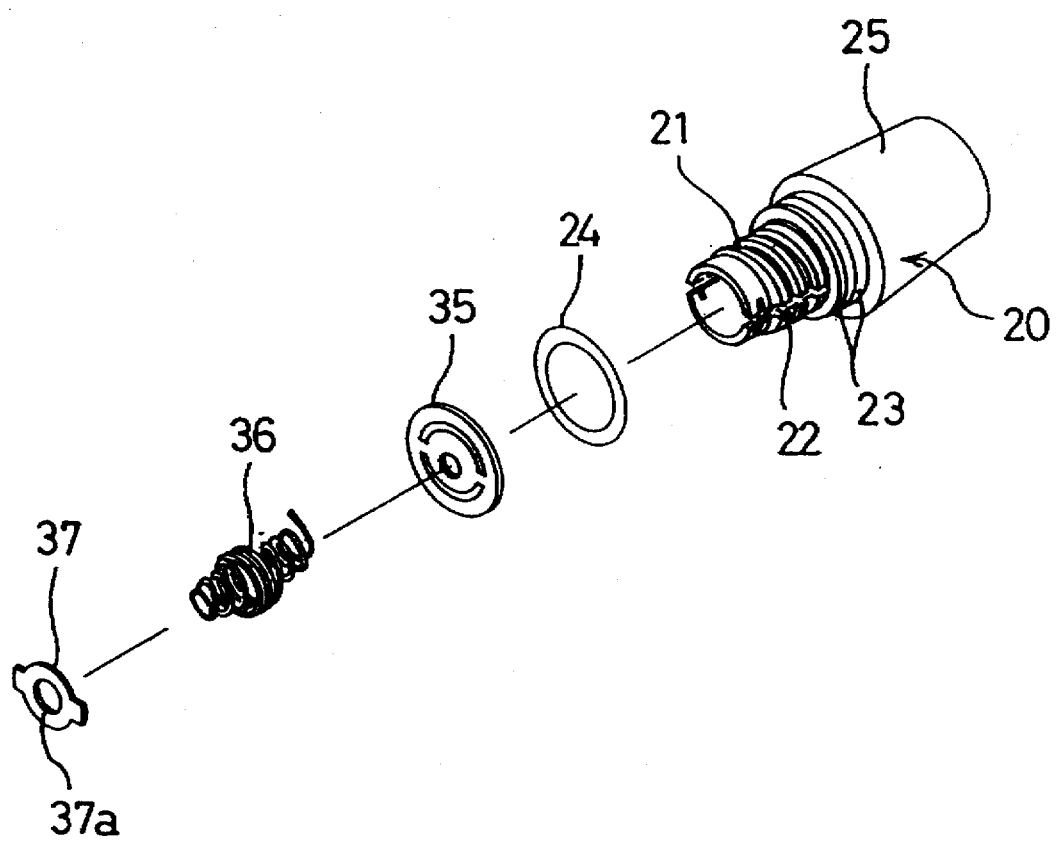

[ Fig. 4 ]
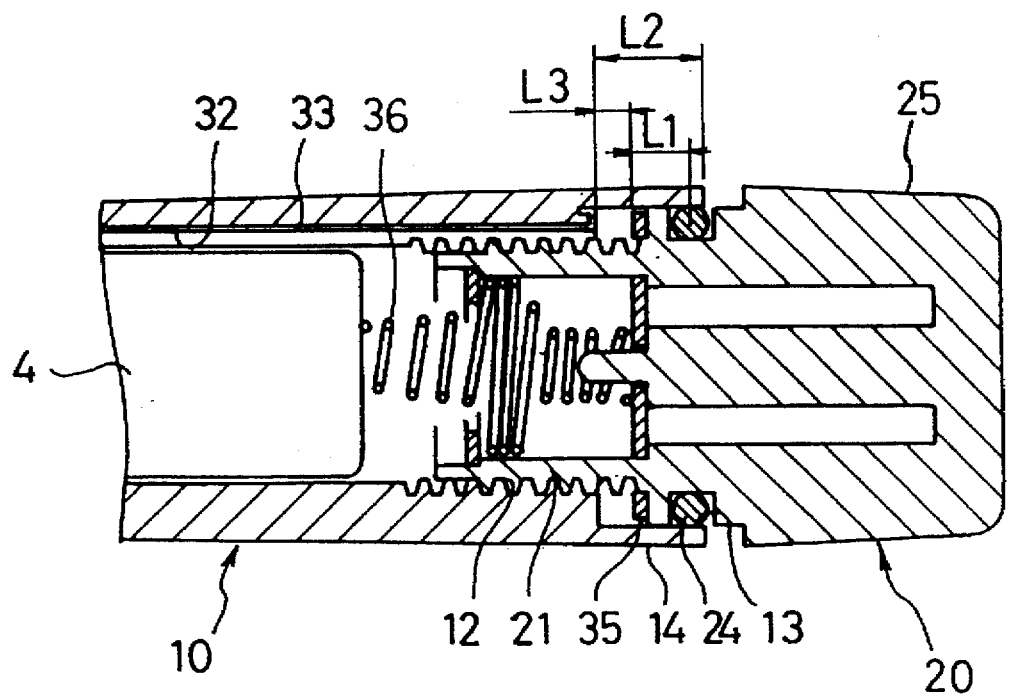
[ Fig. 5 ]
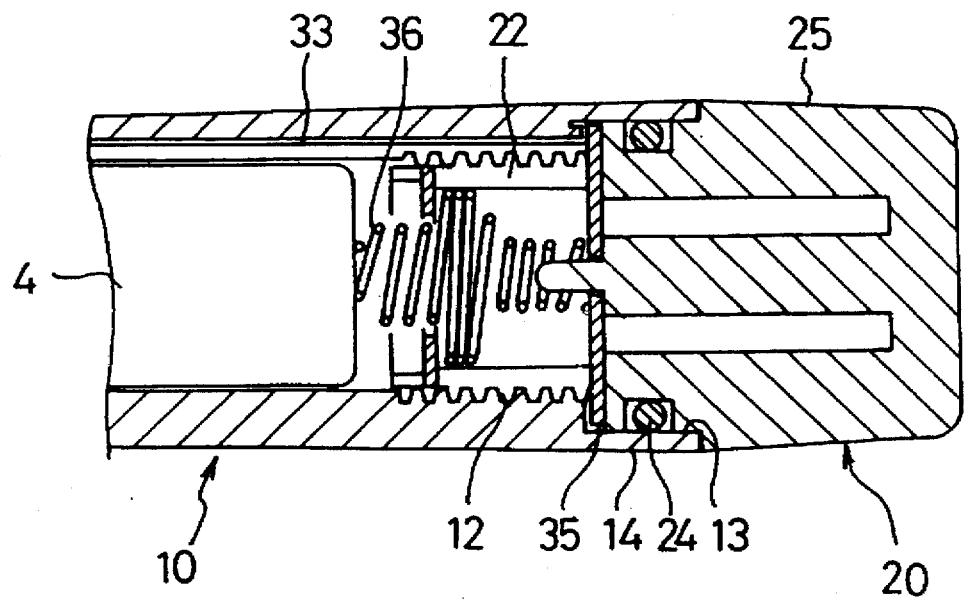

[ Fig. 6 ]
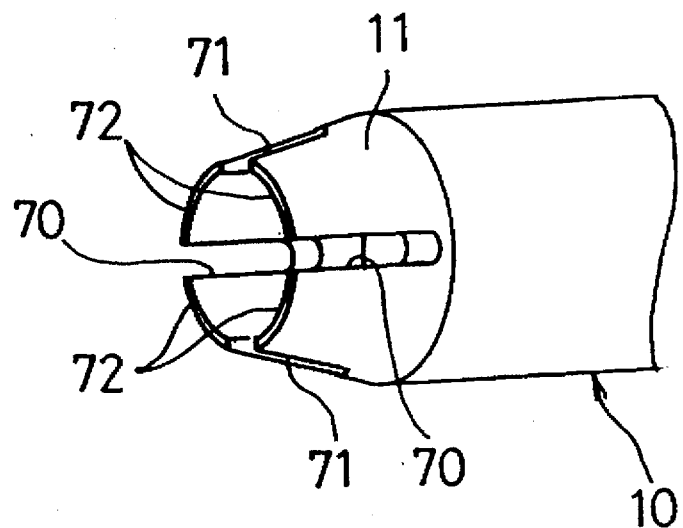
[ Fig. 7 ]
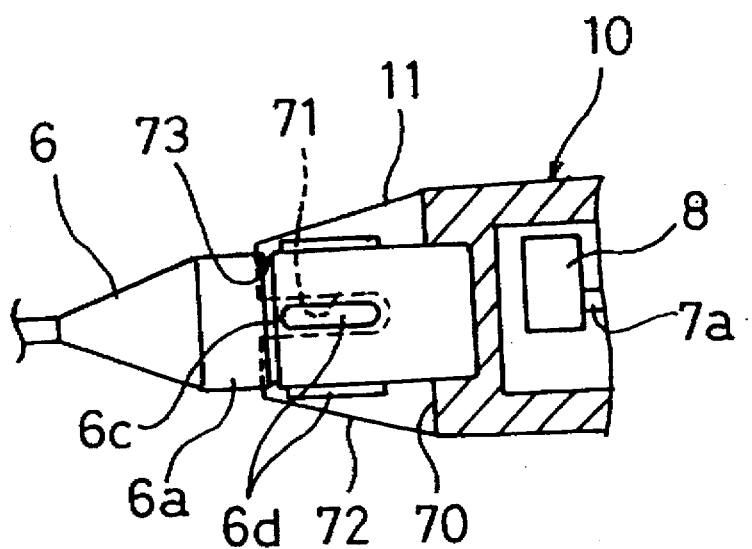

[ Fig. 8 ]
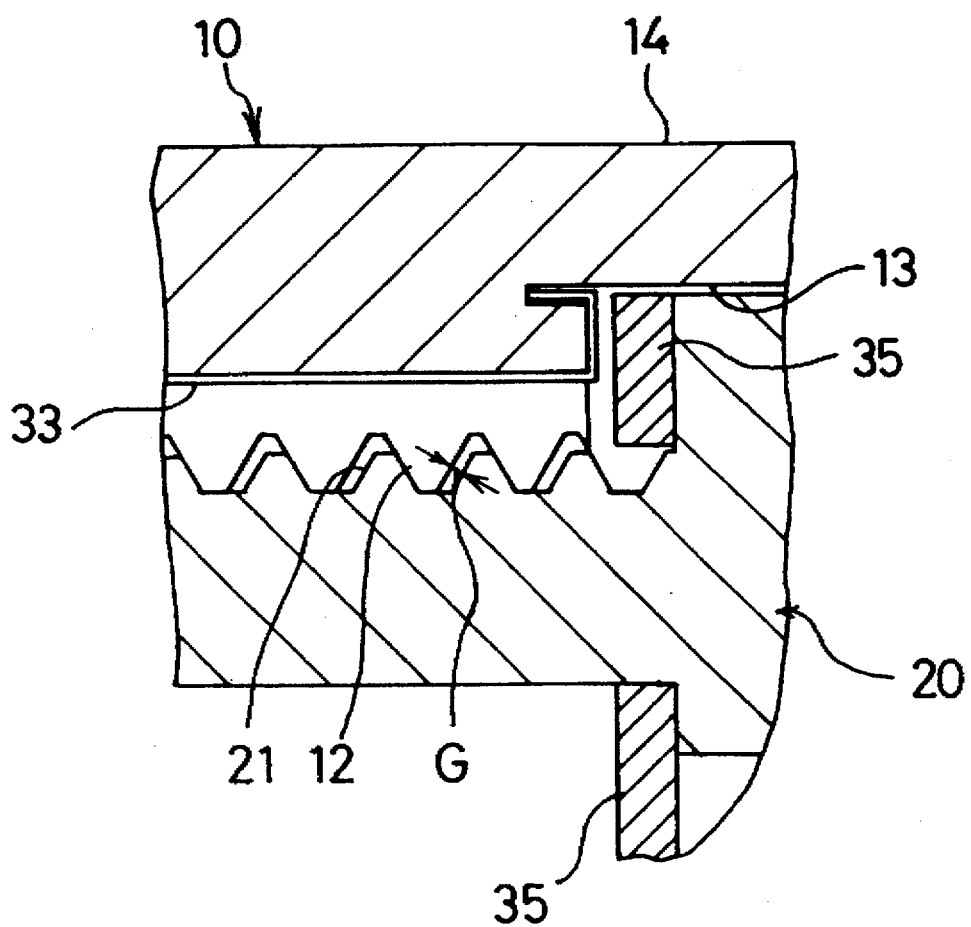

【 Fig. 9 】
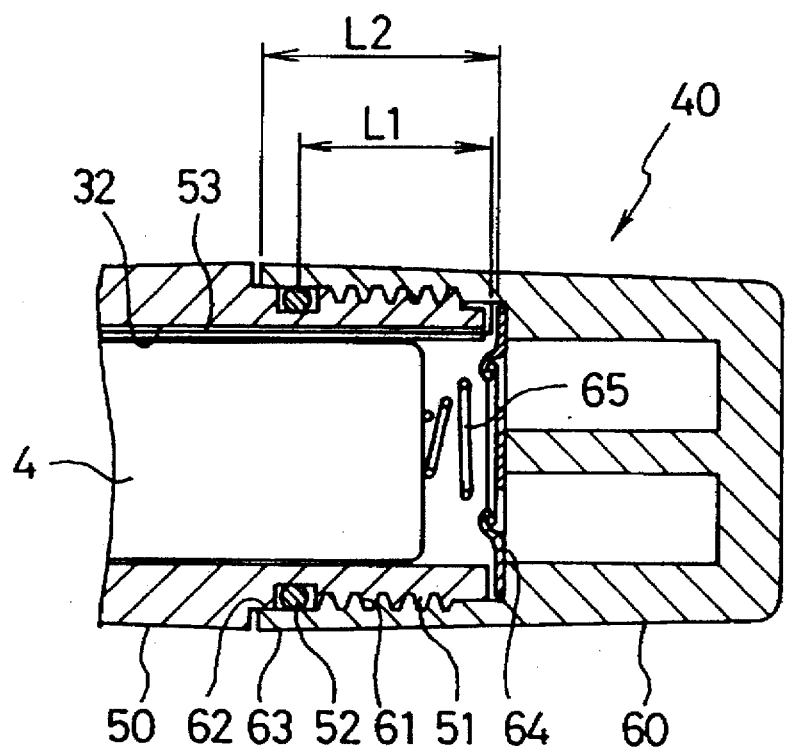
【 Fig.10 】
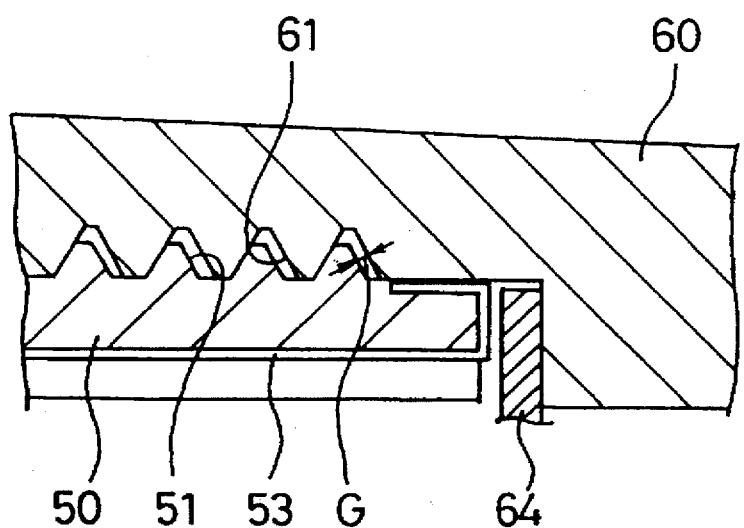

[ Fig.12 ]
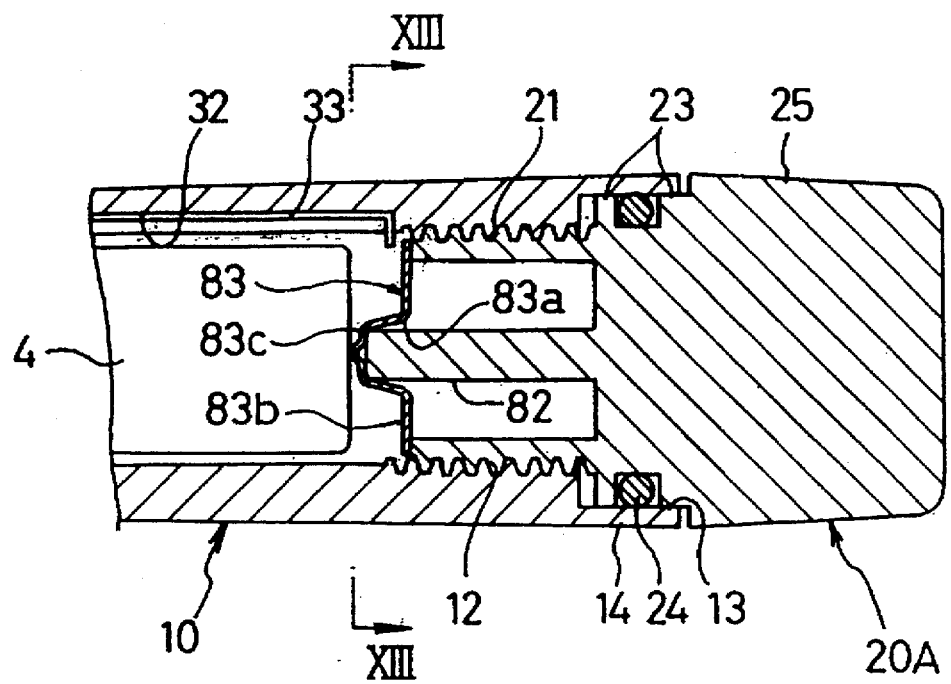
[ Fig.13 ]
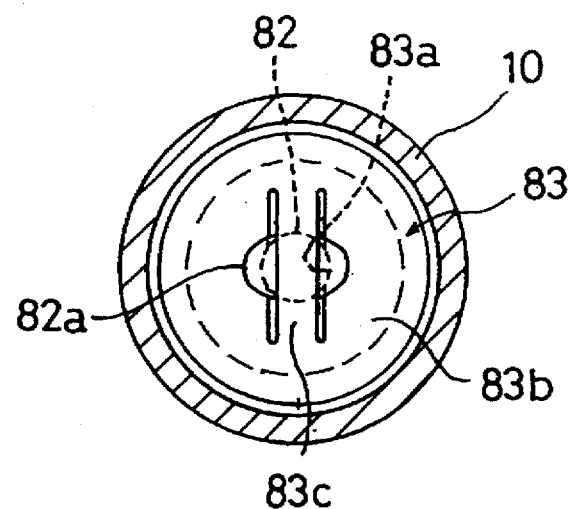

[ Fig.14 ]
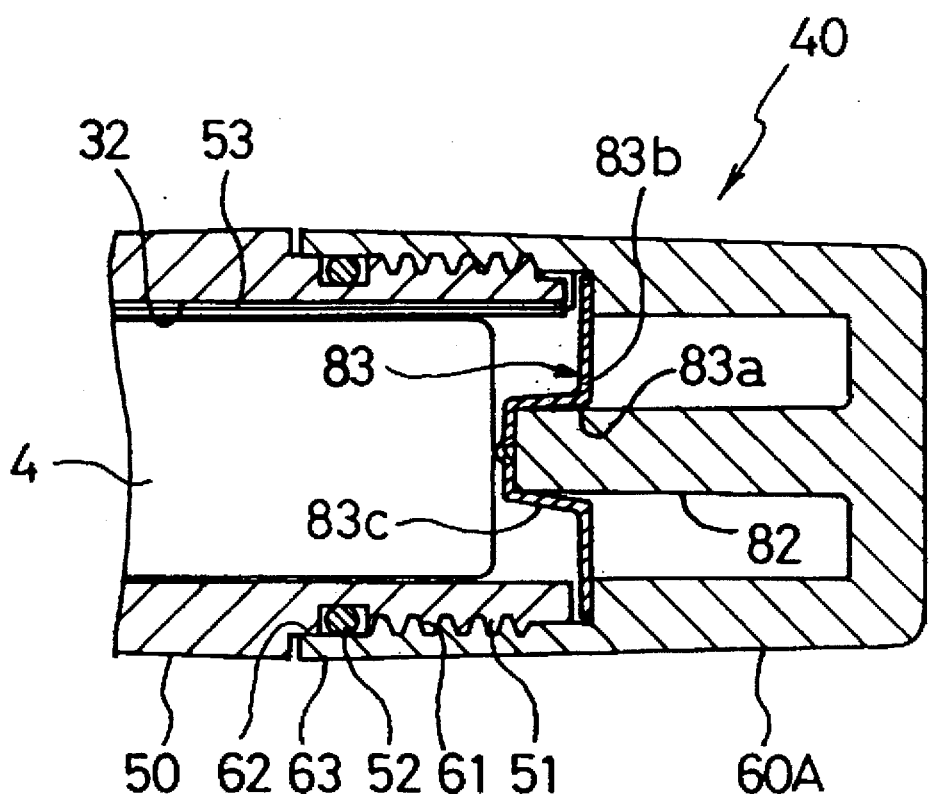

[ Fig.15 ]
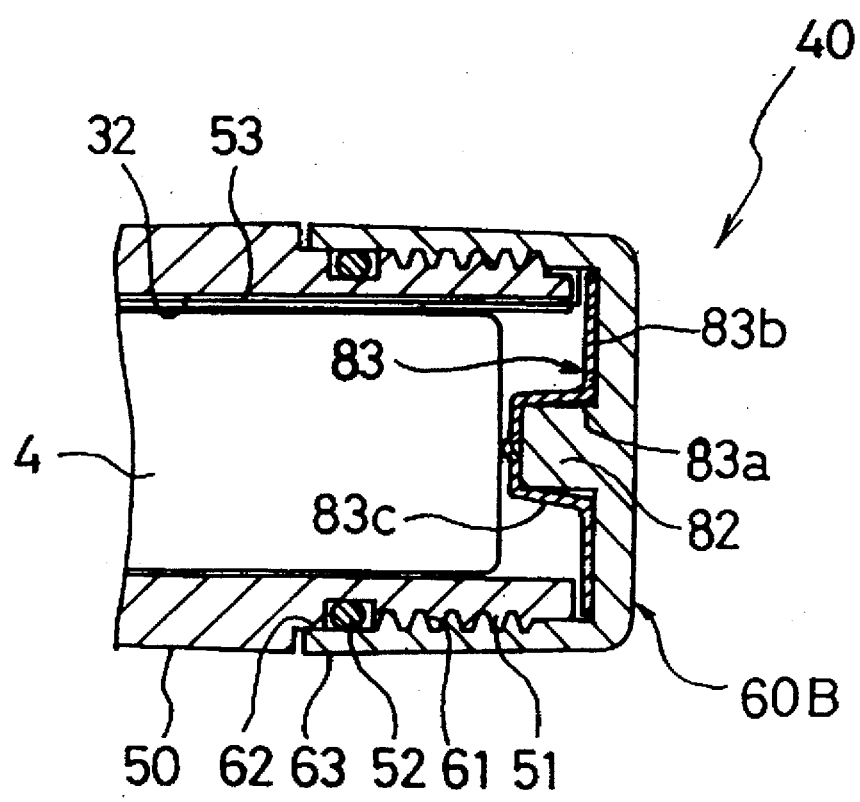

【 Fig.16 】
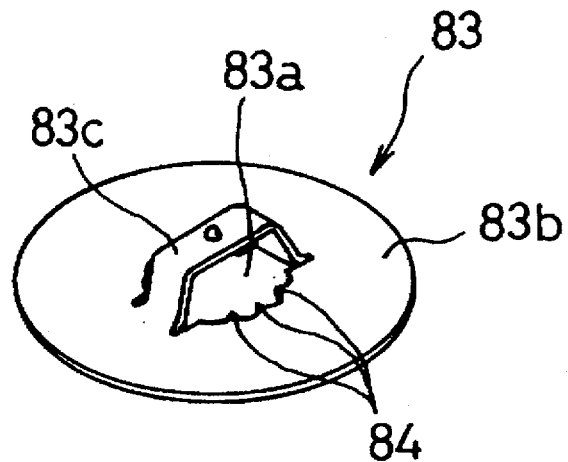
【 Fig.17 】
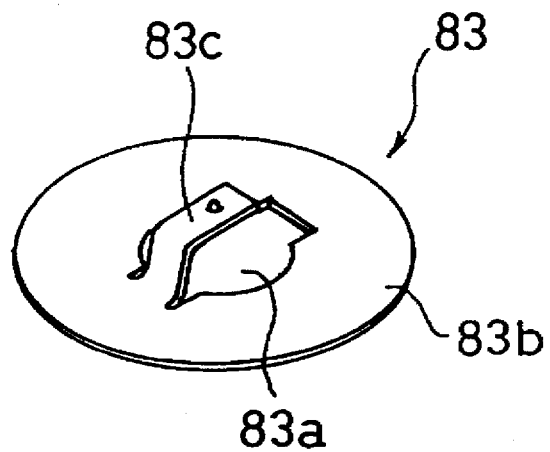

[ Fig.18 ]
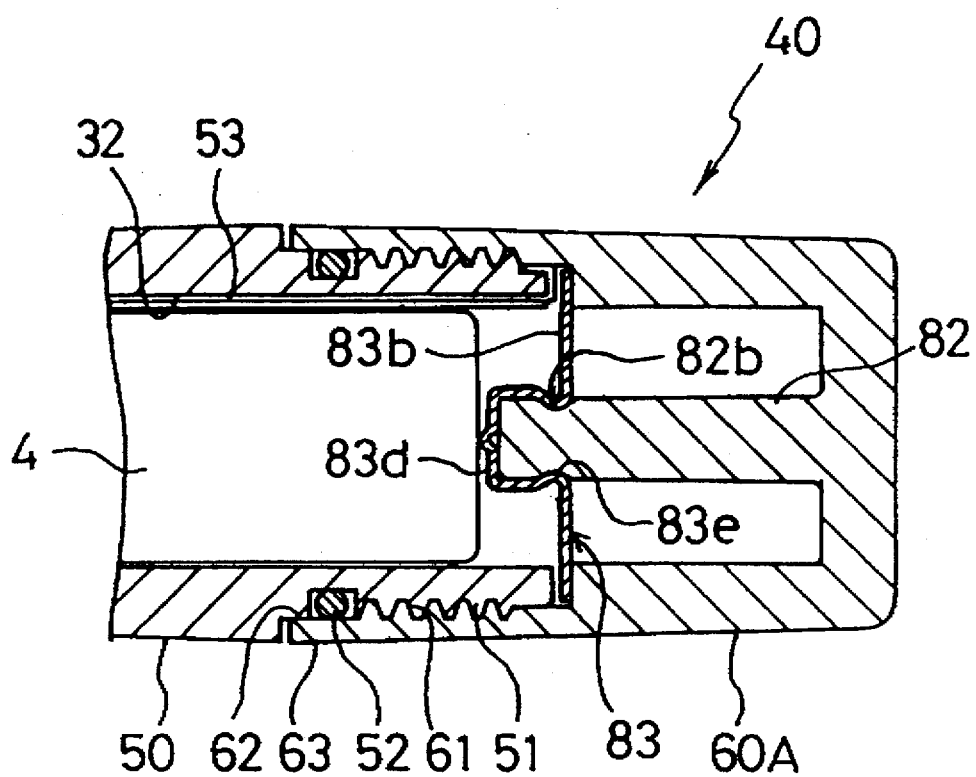

[ Fig.19 ]
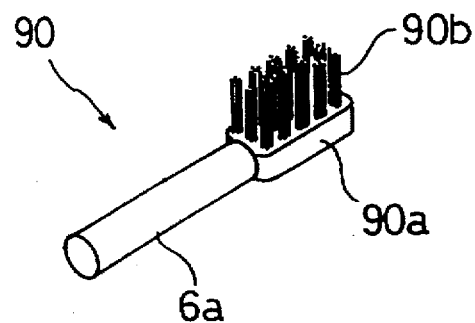
[ Fig.20 ]
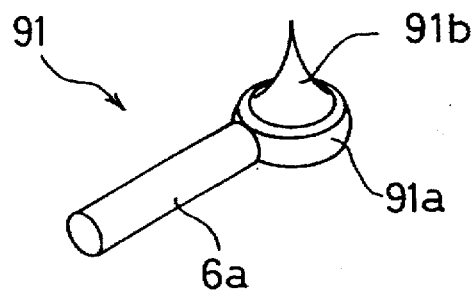
[ Fig.21 ]
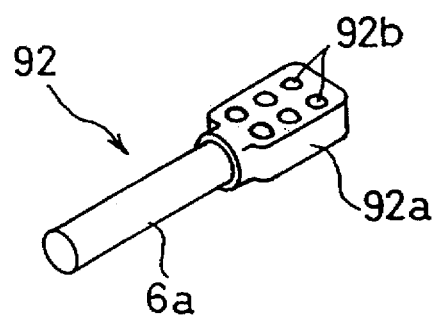
[ Fig.22 ]
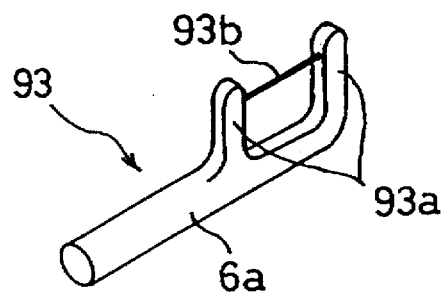

【 Fig.23 】
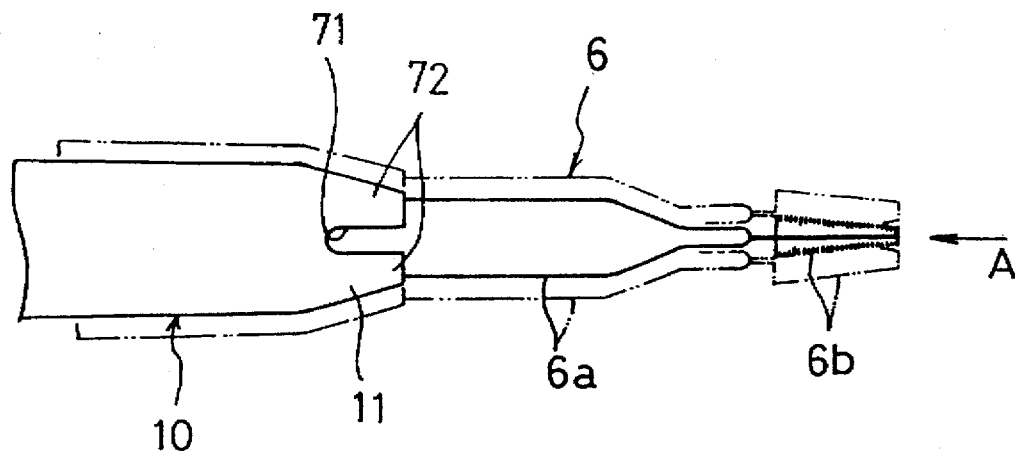
【 Fig.24 】
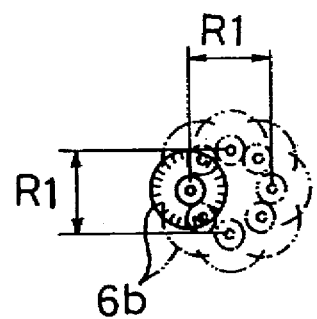

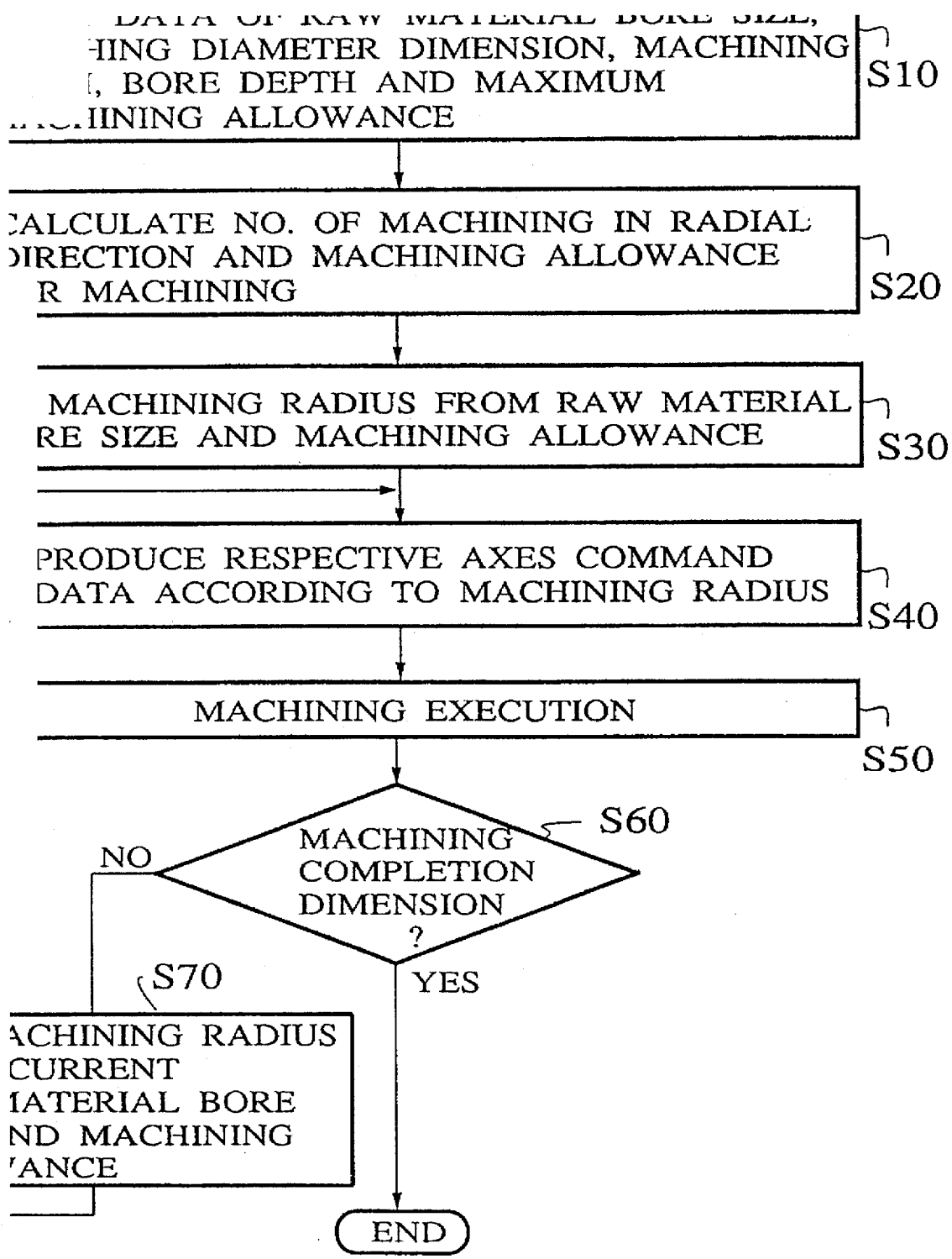

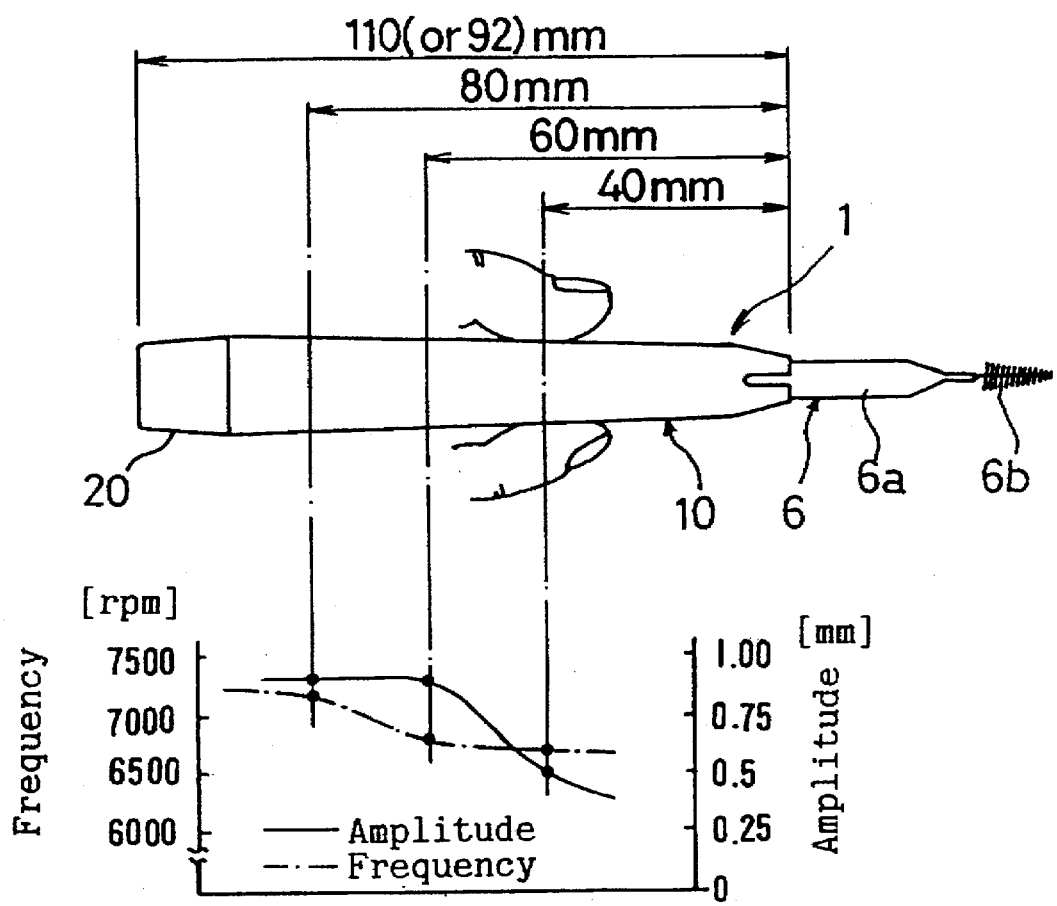
[ Fig.27 ]

[ Fig.28 ]
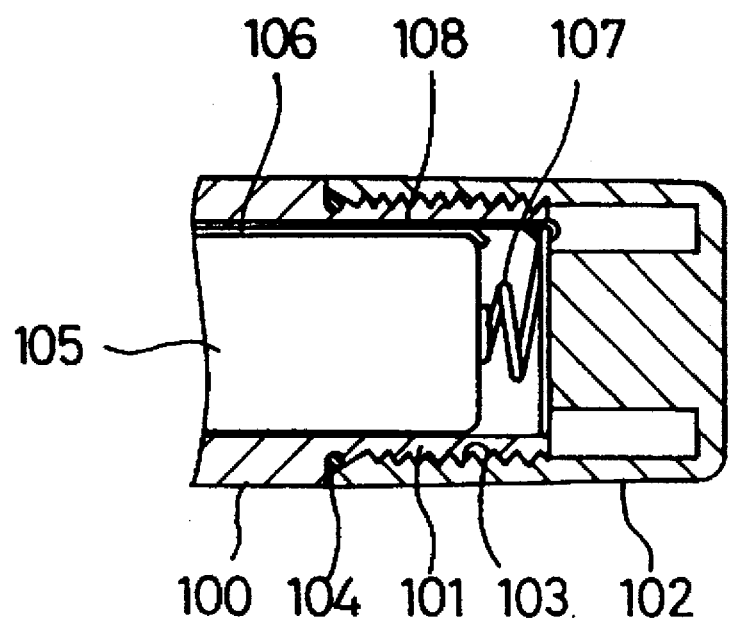

5,718,667

ORAL HYGIENE INSTRUMENT

TECHNICAL FIELD

This invention relates to a portable oral hygiene instrument such as an electric interdental brush, an electric toothbrush or an electric gum massager.

BACKGROUND ART

Various electric toothbrushes and electric interdental cleaning brushes which have an interdental cleaning brush or a toothbrush removably attached to one end of a substantially cylindrical holder member and an electric motor and a battery for powering the same mounted inside the holder member and have the other end of the holder member watertightly sealed by a cap member and have an eccentric weight fixed to the rotary shaft of the electric motor and vibrate the interdental cleaning brush by way of the holder member with vibration generated by rotation of the eccentric weight have been proposed.

Because electric toothbrushes and electric interdental cleaning brushes are usually used in bathrooms and the like they are required to be watertight, and in their construction, for example as shown in FIG. 28, a female thread portion 103 of a cap member 102 is screwed onto a male thread portion 101 of a holder member 100, a seal ring 104 is fitted around the base of the male thread portion 101, and by the cap member 102 being screwed onto the holder member 100 the seal ring 104 is pressed upon by the end of the cap member 102 and the gap between the holder member 100 and the cap member 102 is sealed; to supply electricity to an electric motor, the positive pole of a battery 105 is directly connected to one of the terminals of the electric motor and the other terminal of the electric motor is extended by way of a bandlike wiring plate 106 or the like to the vicinity of an opening in the holder member 100, the negative pole of the battery 105 is connected to a spring terminal 107 mounted in the cap member 102, a bandlike connecting plate 108 connected to the spring terminal 107 is mounted between the wiring plate 106 and the circumferential wall of the holder member 100 and electrically connects the spring terminal 107 to the wiring plate 106, a switch is interposed in this supply circuit and the motor is operated by operating the switch.

However, with the kind of electric toothbrush or electric interdental cleaning brush described above, because even when the cap member has become somewhat loose the supply circuit is closed and if the switch is operated the electric motor will operate, there has been the problem that the instrument is sometimes used without it being noticed that the cap member is loose and water or the like gets inside the holder member and corrodes the electric motor and the battery and the wiring, etc.

Also, after the switch is turned OFF without it being noticed that the cap member is loose, the whole device is sometimes washed in order to clean it or is just left with toothbrushing water still on it. At such times, as well as water getting in and corroding the wiring plate and the electric motor and the battery, eventually causing the instrument to break down, the problem has occurred that hardening of the toothbrushing water causes the thread portion of the cap member to get stuck, whereupon the cap member cannot be opened and closed.

Also, in the electric interdental cleaning brush described above, because a spring terminal is mounted on the cap member side and for example a disclike fixing member having a claw portion on its upper surface is provided and with a base portion of the spring terminal held by the claw portion of the fixing member the spring terminal and the fixing member are fitted and fixed to the inner bottom portion of the cap member together, the number of parts increases and installation of the spring terminal in the cap member is extremely complicated.

In order to removably attach an oral hygiene tool such as a toothbrush or an interdental cleaning brush to the holder member the oral hygiene tool is usually provided with a shaft portion and a fitting hole is formed in one end of this shaft portion and the oral hygiene tool is removably attached to the holder member by this fitting hole being fitted over a projecting portion formed on the holder member, or the oral hygiene tool is removably attached to the holder member by the base portion of the shaft portion being plugged into a bottomed cylindrical holding portion formed in the holder member. Also, sometimes a plurality of axial slits are formed in the holding portion so that the end of the holding portion can expand and contract radially and absorb dimensional errors in the outer diameter of the shaft portion and also so that toothpaste powder adhered to the inner back surface of the holding portion can be easily cleaned off. However, when slits are thus provided in the holding portion, if the slits are made long the force with which the shaft portion is held decreases; consequently it is problematic to have the slits extending as far as the vicinity of the inner back surface of the holding portion and even when slits are provided it cannot be said that toothpaste powder adhered to the inner back surface of the holding portion can be sufficiently effectively cleaned off.

An object of this invention is to provide an oral hygiene instrument in which incursion of water and the like into the holder member due to looseness of the cap member is completely prevented, installation of the spring terminal is simplified, and, while maintaining sufficient strength of attachment of the oral hygiene tool to the holding member, cleaning of the inner back surface of the holding member is easy.

DISCLOSURE OF THE INVENTION

An oral hygiene instrument according to claim 1 comprises: a holder member capable of accommodating a battery and provided with a holder side thread portion at a first end and watertightly closed at a second end; an oral hygiene tool removably attached to the second end of the holder member and comprising a toothbrush or an interdental cleaning brush or a gum massaging tool or a nipple-type gum massaging tool mounted on the end of a shaft portion; vibration generating means housed in the second end of the holder member for vibrating the oral hygiene tool by way of the holder member; a cap member having a cap side thread portion meshing with the holder side thread portion which cap member is removably attached to the first end of the holder member and closes an opening in the first end of the holder member; a seal ring fitted on a portion of the holder member or the cap member at the external end of the part where the two members mesh which seal ring is pressed upon by either the cap member or the holder member and seals the gap between the holder member and the cap member within a range of a predetermined angle of screwing of the cap member with respect to the holder member from a late stage to completion of said screwing; and a holder side contact piece and a cap side contact piece mounted in the holder member and the cap member respectively which approach each other when the cap member is screwed with respect to the holder member and in the range of the predetermined angle make contact and close a circuit supplying electricity to the vibration generating means.

In an oral hygiene instrument according to claim 1, within the range of the predetermined angle of screwing of the cap member with respect to the holder member from the late stage to the completion of said screwing the seal ring fitted on the holder member or the cap member is pressed upon by the cap member or the holder member and the gap between the holder member and the cap member is sealed, and in this range of the predetermined angle the holder side contact piece mounted on the holder member makes contact with the cap side contact piece mounted on the cap member and the circuit supplying power to the vibration generating means is thereby closed and an electric motor or the like of the vibration generating means is driven and the oral hygiene tool is vibrated by way of the holder member. That is, because until the cap member is screwed with respect to the holder member as far as the range of the predetermined angle and the gap between the holder member and the cap member is sealed with certainty by the seal ring the supply circuit cannot be closed and the electric motor or the like cannot be driven, and as a result it is made known to the user that sealing is not being effected properly and the instrument can never be used with the seal in an improper state.

Also, because the seal ring is fitted on a portion of the holder member or the cap member at the external end of the part where the two members mesh, the incursion of toothbrushing water or the like into where the holder member and the cap member mesh is prevented with certainty.

An oral hygiene instrument according to claim 2 is an instrument according to claim 1 wherein the holder side contact piece and the cap side contact piece constitute a switch of the supply circuit, and the supply circuit is opened and closed by the cap member being turned in the range of the predetermined angle.

In an oral hygiene instrument according to claim 2, by turning the cap member within the range of the predetermined angle, the supply circuit can be opened and closed with the gap between the holder member and the cap member sealed with certainty.

An oral hygiene instrument according to claim 3 is an instrument according to claim 1 wherein a switch for opening and closing the supply circuit is provided in the holder member or the cap member.

In an oral hygiene instrument according to claim 3, if the gap between the holder member and the cap member is not sealed properly it is impossible to close the supply circuit even by operating the switch, and it is made known to the user that sealing is not being effected properly.

An oral hygiene instrument according to claim 4 is an instrument according to claim 1 wherein: an axial play is provided between the holder side thread portion and the cap side thread portion; a spring terminal pressed against one electric pole of the battery is provided; and the urging force of this spring terminal urges the cap member away from the holder member.

In an oral hygiene instrument according to claim 4, when the cap member is screwed with respect to the holder member until just before the holder side contact piece and the cap side contact piece make contact and the cap member is then pushed, the supply circuit is closed, and when the pushing of the cap member is ceased the urging force of the spring terminal causes the holder side contact piece to move away from the cap side contact piece and the supply circuit is opened.

An oral hygiene instrument according to claim 5 comprises: a holder member capable of accommodating a battery; a cap member capable of watertightly closing a first end of the holder member; an oral hygiene tool comprising a toothbrush or an interdental cleaning brush or a gum massaging tool or a nipple-type gum massaging tool mounted on the end of a shaft portion; a bottomed cylindrical holding part watertightly closing a second end of the holder member and capable of holding therein the base end of the shaft of the oral hygiene tool and provided with a plurality of first slits extending from the end to the vicinity of the inner back surface of the holding part and a plurality of second slits shorter than the first slits extending from the end toward the inner back surface of the holding part; and vibration generating means housed in the second end of the holder member for vibrating the oral hygiene tool by way of the holder member.

In an oral hygiene instrument according to claim 5, the oral hygiene tool is fixed in the holding portion by the base portion of the shaft portion of the oral hygiene tool being inserted into the holding portion, the vibration generating means is driven and the oral hygiene tool is vibrated by way of the holder member and the holding portion. Because the plurality of first slits and second slits are provided in the holding portion, the end of the holding portion can elastically expand and contract radially relatively greatly, and even if there are relatively large variations in the molding accuracy of the shaft portion the shaft portion can be held with certainty and the oral hygiene tool prevented from falling off, and because the first slits extend to the vicinity of the inner back surface of the holding portion, cleaning off of toothpaste powder and the like clogging the inner back portion of the holding portion is easy.

An oral hygiene instrument according to claim 6 is an instrument according to claim 5 wherein an engaging projection for restricting axial movement of the shaft portion of the oral hygiene tool is provided on the inner circumferential side of a portion of the holding part near the end thereof.

In an oral hygiene instrument according to claim 6, the engaging projection provided on the inner circumferential side of the portion of the holding part near the end thereof engaging with the shaft portion of the oral hygiene tool restricts axial movement of the oral hygiene tool and more effectively prevents it from coming off, and also the efficiency with which vibration is transmitted to the oral hygiene tool is increased.

An oral hygiene instrument according to claim 7 is an instrument according to claim 5 or 6, wherein a protrusion or axial tongue projection for engaging with a first or second slit is provided on the outer circumferential surface of the shaft portion of the oral hygiene tool.

In an oral hygiene instrument according to claim 7, the protrusion or axial tongue projection provided on the outer circumferential surface of the shaft portion of the oral hygiene tool engaging with the first or second slit restricts the rotation of the oral hygiene tool about the shaft portion and the operability of the oral hygiene instrument is further improved.

An oral hygiene instrument according to claim 8 comprises: a holder member capable of accommodating a battery and having a first end open and a second end watertightly closed; a bottomed cylindrical cap member watertightly closing the opening of the first end of the holder member and having a projecting mounting portion provided on a central portion of its inner back surface; an oral hygiene tool removably attached to the second end of the holder member and comprising a toothbrush or an interdental cleaning brush or a gum massaging tool or a nipple-type gum massaging tool mounted on the end of a shaft portion; vibration generating means housed in the second end of the holder member for vibrating the oral hygiene tool by way of the holder member; a holder side contact piece extending axially along the inner wall surface of the holder member and having one end disposed in the vicinity of the first end of the holder member and another end electrically connected to the vibration generating means; a cap side contact piece mounted on the mounting portion and having an annular brim portion fitting around the mounting portion and capable of making sliding contact with the holder side contact piece and a contact portion extending from the brim portion to the front side of the end of the mounting portion; and a spring terminal having a first end electrically connected to the vibration generating means and a second end disposed contactably with a first electric pole of a battery housed in the holder member, wherein when the cap member is fitted to the holder member the second end of the spring terminal is pressed against the first electric pole of the battery and presses a second electric pole of the battery against the contact portion of the cap side contact piece.

In an oral hygiene instrument according to claim 8, because the spring terminal is fitted to the vibration generating means and the cap side contact piece comprising the brim portion and the contact portion is fitted on the cap member, the constitution of the cap member can be greatly simplified and compared to a case wherein a spring terminal is fixed to the cap member the work of installing the spring terminal can be greatly simplified.

An oral hygiene instrument according to claim 9 is an instrument according to claim 8 wherein an engaging projection which engages with the mounting portion is provided projecting inward at an opening portion in the brim portion through which the mounting portion passes.

In an oral hygiene instrument according to claim 9, the cap side contact piece can be fitted to the cap member by the cap side contact piece being press-fitted onto the mounting portion and the engaging projection being caused to engage with the outer circumferential surface of the mounting portion, and the installation of the cap side contact piece is made much easier.

An oral hygiene instrument according to claim 10 is an instrument according to claim 8, wherein the contact portion straddles the end of the mounting portion and the cap side contact piece is fixed to the cap member by a flat portion formed by melting portions of the mounting portion exposed on either side of the contact portion.

In an oral hygiene instrument according to claim 10, because with the cap side contact piece fitted to the mounting portion a flat portion is formed by melting the portions of the mounting portion exposed on either side of the contact portion, it is possible to easily fix the cap side contact piece to the cap member.

An oral hygiene instrument according to claim 11 comprises: a holder member provided at a first end thereof with a holder side thread portion and capable of accommodating a battery; a bottomed cylindrical cap member fitted to the first end of the holder member and closing an opening of the first end of the holder member and provided at an end thereof with a cap side thread portion mating with the holder side thread portion and having a mounting portion projecting from a central portion of an inner back surface thereof; an oral hygiene tool comprising a toothbrush or an interdental cleaning brush or a gum massaging tool or a nipple-type gum massaging tool or the like mounted on a shaft portion; a bottomed cylindrical holding part watertightly closing a second end of the holder member and capable of holding therein the base end of the shaft of the oral hygiene tool and provided with a plurality of first slits extending from the end to the vicinity of the inner back surface of the holding part and a plurality of second slits shorter than the first slits extending from the end toward the inner back surface of the holding part; vibration generating means housed in the second end of the holder member for vibrating the oral hygiene tool by way of the holder member; a seal ring fitted on a portion of the holder member or the cap member at the external end of the part where the two members mesh which seal ring is pressed upon by either the cap member or the holder member and seals the gap between the holder member and the cap member within a range of a predetermined angle of screwing of the cap member with respect to the holder member from a late stage to completion of said screwing; a holder side contact piece extending axially along the inner wall surface of the holder member and having one end disposed in the vicinity of the first end of the holder member and another end electrically connected to the vibration generating means; a cap side contact piece mounted on the mounting portion and having an annular brim portion fitted around the mounting portion and a contact portion extending from the brim portion to the front side of the end of the mounting portion, the cap member being screwed with respect to the holder member causing the brim portion to approach the holder side contact piece and in the range of the predetermined angle make contact with the holder side contact piece and close a circuit supplying electricity to the vibration generating means; and a spring terminal having a first end electrically connected to the vibration generating means and a second end disposed contactably with a first electric pole of a battery housed in the holder member, wherein when the cap member is fitted to the holder member the second end of the spring terminal is pressed against the first electric pole of the battery and presses a second electric pole of the battery against the contact portion of the cap side contact piece.

In an oral hygiene instrument according to claim 11, as in that of claim 1, because until the cap member is screwed with respect to the holder member as far as the range of the predetermined angle and the gap between the holder member and the cap member is sealed with certainty by the seal ring the supply circuit cannot be closed and the electric motor or the like cannot be driven, as a result it is made known to the user that sealing is not being effected properly and the incursion of toothbrushing water or the like into where the holder member and the cap member mesh is prevented with certainty by the seal ring. Also, as in the instrument of claim 5, because a plurality of first slits and second slits are provided in the holding portion, the end of the holding portion can elastically expand and contract radially relatively greatly, and even if there are relatively large variations in the molding accuracy of the shaft portion the shaft portion can be held with certainty and the oral hygiene tool prevented from falling off, and because the first slits extend to the vicinity of the inner back surface of the holding portion, cleaning off of toothpaste powder and the like clogging the inner back portion of the holding portion is easy. Also, as in the instrument of claim 8, because the spring terminal is fitted to the vibration generating means and the cap side contact piece comprising the brim portion and the contact portion is fitted on the cap member, the constitution of the cap member can be greatly simplified and compared to a case wherein a spring terminal is fixed to the cap member the work of installing the spring terminal can be greatly simplified.

BRIEF DESCRIPTION OF THE DRAWINGS

FIG. 2 is a vertical sectional detail view of the electric interdental cleaning brush;

FIG. 3 is a perspective view of a cap member and members fitted therein;

FIG. 4 is a view corresponding to FIG. 2 showing a position of a seal ring having just started sealing;

FIG. 5 is a view corresponding to FIG. 2 showing the state when a supply circuit has been switched ON;

FIG. 6 is a perspective view of the vicinity of a holding portion of a holder member;

FIG. 7 is a vertical sectional view of a holding portion and a modified shaft portion;

FIG. 8 is a vertical sectional detail view of modified male and female thread portions;

FIG. 9 is a view corresponding to FIG. 2 showing part of an electric interdental cleaning brush according to a first other preferred embodiment;

FIG. 10 is a vertical sectional detail view of modified male and female thread portions of the first other preferred embodiment;

FIG. 12 is a view corresponding to FIG. 2 of part of the electric interdental cleaning brush according to the second other preferred embodiment;

FIG. 13 is a sectional view on the line XIII—XIII in FIG. 12;

FIG. 14 is a view corresponding to FIG. 9 of part of an electric interdental cleaning brush according to a third other preferred embodiment;

FIG. 15 is a view corresponding to FIG. 14 of a modified cap member of the electric interdental cleaning brush according to the third other preferred embodiment;

FIG. 16 is a perspective view showing a modified cap side contact piece;

FIG. 17 is a perspective view showing a modified cap side contact piece;

FIG. 18 is a view corresponding to FIG. 14 of a modified cap side contact piece;

FIG. 19 is a perspective view of a toothbrush constituting an oral hygiene tool;

FIG. 20 is a perspective view of a nipple-type gum massager constituting an oral hygiene tool;

FIG. 21 is a perspective view of a gum massager constituting an oral hygiene tool;

FIG. 22 is a perspective view of a floss unit constituting an oral hygiene tool;

FIG. 23 is a view illustrating a vibration mode of an interdental cleaning brush;

FIG. 24 is a view in the direction of the arrow A in FIG. 23;

FIG. 25 is a view illustrating a vibration mode of an interdental cleaning brush in a bent state;

FIG. 26 is a view in the direction of the arrow B in FIG. 25;

FIG. 27 is a view illustrating a relationship between holding position and vibration frequency; and FIG. 28 is a vertical sectional detail view of an example of a conventional electric interdental cleaning brush.

BEST MODES FOR CARRYING OUT THE INVENTION

Preferred embodiments of the invention will now be described with reference to the accompanying drawings.

In these preferred embodiments the invention is applied to a portable electric interdental cleaning brush.

Figure 1:
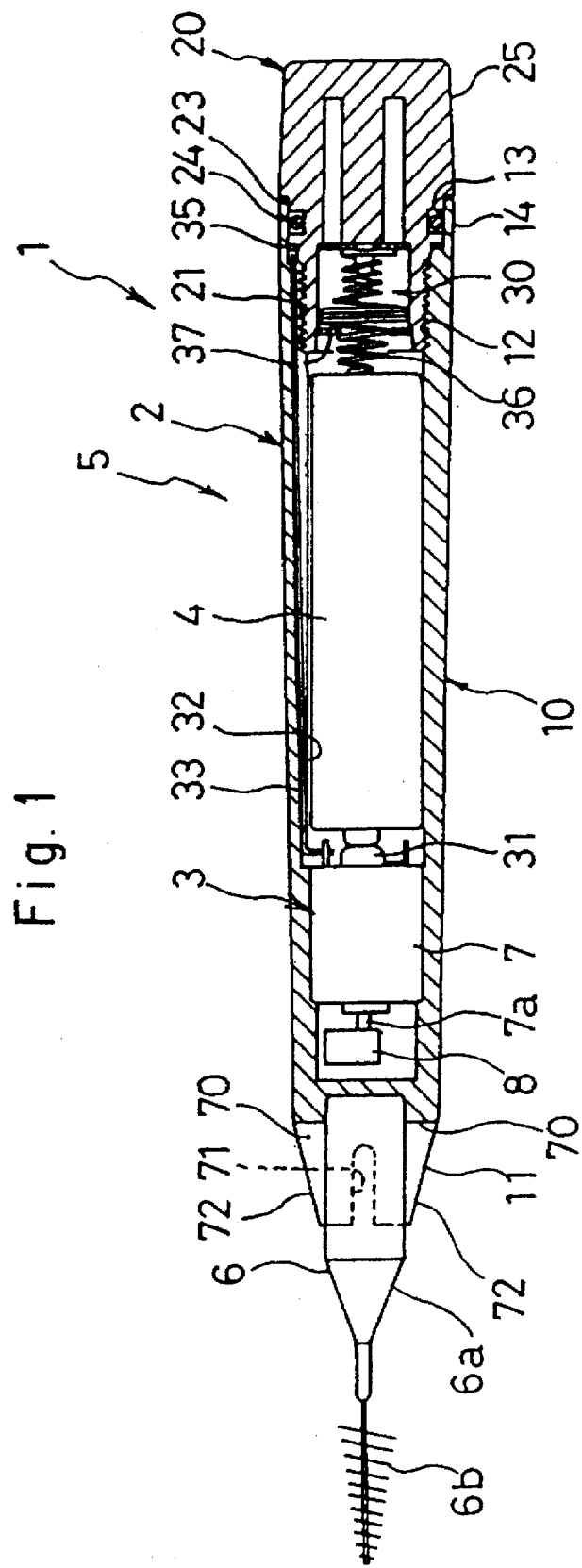
FIG. 1 is a vertical sectional view of an electric interdental cleaning brush.

Referring to FIG. 1, a portable electric interdental cleaning brush 1 comprises a device proper 5 made up of vibration generating means 3 and a battery 4 housed in a watertight battery holder 2 and an interdental cleaning brush 6 constituting an oral hygiene tool removably fitted to the left hand end portion of the device proper 5. Other oral hygiene tools which will be further discussed later such as a tooth brush 90, a nipple-type gum massaging tool 91, a gum massaging tool 92 or a floss unit 93 can be fitted to the device proper 5.

The waterproof battery holder 2 comprises a substantially cylindrical holder member 10 housing the vibration generating means 3 and the battery 4, a cap member 20 removably fitted to the holder member 10 and wiring means 30 constituting a circuit supplying electricity to the vibration generating means 3. The holder member 10 and the cap member 20 are made of an insulating synthetic resin material.

As shown in FIG. 1 and FIG. 2, the holder member 10 is a cylindrical member closed near its left hand end; a holding portion 11 for removably holding the interdental cleaning brush 6 is formed at the left hand end of the holder member 10; a female thread portion 12 is formed on the inner wall of a portion of the holder member 10 near the right hand end thereof, and a seal portion 14 having a seal surface 13 of larger diameter than the female thread portion 12 is formed on the inside of the right hand end portion of the holder member 10.

As shown in FIG. 1 to FIG. 3, the cap member 20 is a substantially cylindrical member whose right hand end is closed; a male thread portion 21 which screws into the female thread portion 12 is formed on a left portion of the cap member 20; this male thread portion 21 is divided into two halves by a pair of slits 22 extending in the left-right direction; a fitting portion 23 of greater diameter than the male thread portion 21 is formed to the right side of the male thread portion 21 (the external side of the end of the meshing of the female thread portion 12 and the male thread portion 21); a seal ring 24 compressed to form a watertight seal by the seal surface 13 is fitted in the fitting portion 23, and a grip portion 25 of greater diameter than the fitting portion 23 for the user to grip when turning the cap member 20 is formed on the right hand end of the cap member 20.

As shown in FIG. 1, the vibration generating means 3 comprises an electric motor 7 mounted in the left hand end vicinity of the holder member 10 and an eccentric weight 8 fixed to a rotary shaft 7a projecting to the left from the electric motor 7, and vibrates the interdental cleaning brush 6 by causing a centrifugal force exerted by the eccentric weight 8 to act on the holder member 10.

Describing now the wiring means 30, as shown in FIG. 1 to FIG. 3 a cuplike contact piece 31 which makes contact with the positive pole of the battery 4 is mounted on the right hand end of the electric motor 7 covering the rotary shaft 7a and is connected to one of the terminals of the electric motor 7; a groove portion 32 extending in the left-right direction is formed in the inner wall of the holder member 10, a bandlike holder side contact piece 33 connected to the other terminal of the electric motor 7 is mounted in the groove portion 32, and the right hand end of the holder side contact piece 33 extends into the seal portion 14 and engages with an annular step 34 between the seal portion 14 and the female thread portion 12.

A substantially disclike cap side contact piece 35 is fixed to the cap member 20 at the base of the male thread portion 21, and an outer circumferential portion of the cap side contact piece 35 faces the right hand end portion of the holder side contact piece 33; a spring terminal 36 consisting of a coil spring of enlarged diameter around its central portion is received in the male thread portion 21; a portion of the spring terminal 36 part-way therealong is restrained by a restraining piece 37 fixed in the vicinity of the left hand end of the male thread portion 21; the right hand end of the spring terminal 36 is electrically connected to the cap side contact piece 35, and the left hand end of the spring terminal 36 passes through a through hole 37a formed in the restraining piece 37 and makes pressure contact with the negative pole of the battery 4.

The holder side contact piece 33 and the cap side contact piece 35 constitute the contacts of a switch of the supply circuit; as shown in FIG. 4, the distance L1 between the left end surface of the cap side contact piece 35 and the center of the seal ring 24 is by design shorter than the distance L2 between the right end surface of the holder side contact piece 33 and the right end surface of the seal portion 14; when the cap member 20 is screwed into the holder member 10 and the periphery of the seal ring 24 in the seal portion 14 is first pressed upon by the seal surface 13, the holder side contact piece 33 and the cap side contact piece 35 are a clearance L3 apart; as shown in FIG. 5, when the cap member 20 is screwed further into the holder member 10 the cap side contact piece 35 is pressed against the holder side contact piece 33 and the supply circuit is closed and the electric motor 7 is driven.

It has been found in monitor tests that here the required operation angle through which the cap member 20 must be turned to bring the cap side contact piece 35 and the holder side contact piece 33 into and out of contact, i.e. the operation angle required to turn the supply circuit ON or OFF, is 90° to 150°, and the clearance L3 is set to above the pitch of the thread portions multiplied by 150°/360° and preferably above the value of when the operation angle is set to above 360° to 450°. That is, by setting L3 as large as possible within the range over which L3+L1 does not exceed L2, the range of the sealing effect can be widened.

As shown in FIG. 1 and FIG. 6, the holding portion 11 is a bottomed cylindrical member so formed integrally with the holder member 10 that it closes off the left hand end of the holder member 10 and is conelike, contracting with progress toward the left; a pair of first slits 70 and a pair of second slits 71 are formed alternately in the left portion of the holding portion 11, uniformly circumferentially spaced therearound; the first slits 70 are formed from the left hand end of the holding portion 11 to the vicinity of the inner back surface, and the second slits 71 are formed from the left hand end of the holding portion 11 to part-way down the holding portion 11; four claws 72 are formed by the slits 70 and 71 in the left portion of the holding portion 11. A different number of slits from that described above may be provided.

As shown in FIG. 1, the interdental cleaning brush 6 comprises a shaft portion 6a made of synthetic resin or synthetic rubber or metal or the like which is removably attached to the holding portion 11 and a brush portion 6b for interdental cleaning extending to the left from the shaft portion 6a; the brush portion 6b consists of synthetic resin filaments embedded in a steel wire, and the brush portion 6b is fixed to the shaft portion 6a by the right hand end of this steel wire being embedded in the left hand end of the shaft portion 6a.

Because the wall thickness of the holding portion 11 increases with progress toward the inner back surface of the holding portion 11, and also because the second slits 71 only extend to part-way along the holding portion 11, strength of the base portions of the four claws 72 is amply secured. Because the first slits 70 and the second slits 71 are provided, the left hand ends of the claws 72 can radially expand and contract elastically relatively greatly. As a result, even if there is relatively large variation in the molding accuracy of the shaft portion 6a, the holding portion 11 can hold the shaft portion 6a firmly and effectively prevent the interdental cleaning brush 6 from falling out. Also, because the first slits 70 extend as far as the inner back surface vicinity of the holding portion 11, toothpaste powder and the like clogging the inner back portion of the holding portion 11 can be easily cleaned off.

Here, as shown in FIG. 7, a discontinuous annular engaging projection 73 may be provided around the inner surface of the left end vicinity portion of the claws 72, and an annular groove 6c for engaging with the engaging projection 73 may be formed part-way along the shaft portion 6a. In this case, engagement of the engaging projection 73 and the annular groove 6c effectively prevents the interdental cleaning brush 6 held in the holding portion 11 from falling out, and falling out of the interdental cleaning brush 6 is prevented even when the shaft portion 6a is made of a hard synthetic resin or metal. When the shaft portion 6a is made of an elastomer or rubber material, the annular groove 6c can be dispensed with and falling out of the interdental cleaning brush 6 effectively prevented by the engaging projection 73 being allowed to bite into the shaft portion 6a.

As shown in FIG. 7, tongue portions 6d which can engage with the first slits 70 or the second slits 71 can be provided on the base end portion of the shaft portion 6a. In this case, the interdental cleaning brush 6 can be fitted to the portable interdental brush 1 in such a state that it cannot rotate and the operability of the interdental cleaning brush 6 increases. Protrusions may be provided instead of the tongue portions 6d.

Next, the operation of the electric interdental cleaning brush 1 will be described.

When the cap member 20 is screwed into the holder member 10, first, as shown in FIG. 4, the seal ring 24 is pressed upon by the seal surface 13 and the interior of the holder member 10 is thereby watertightly sealed; when the cap member 20 is further screwed in through a predetermined angle, as shown in FIG. 5, with the interior of the holder member 10 thus watertightly sealed, the cap side contact piece 35 is pressed against the holder side contact piece 33, the supply circuit is closed, the electric motor 7 is driven and the interdental cleaning brush 6 is vibrated.

When the cap member 20 is turned through 90° to 150° in the opposite direction, as shown in FIG. 2, the cap side contact piece 35 moves away from the holder side contact piece 33 and the electric motor 7 stops. At this time, the seal ring 24 is kept pressed against the seal surface 13 and the interior of the holder member 10 is kept watertight. Furthermore, in this state, rotation of the cap member 20 is restricted by the seal ring 24 being pressed upon by the seal surface 13, and accidental operation of the electric motor 7 and detachment of the cap member 20 are prevented. From the next time, the supply circuit is switched ON and OFF by the cap member 20 being turned between the state shown in FIG. 5 and the state shown in FIG. 2.

Because thus over the range of turning of the cap member 20 which switches power to the electric motor 7 ON and OFF the gap between the cap member 20 and the holder member 10 is sealed by the seal ring 24, the interior of the holder member 10 can be kept watertight at all times. Furthermore, when the electric interdental cleaning brush 1 is being used, even when the cap member 20 has become loose and the gap between the cap member 20 and the holder member 10 is not being sealed properly by the seal ring 24, to operate the electric motor 7 it is necessary to turn the cap member 20 as shown in FIG. 5, and because the gap between the cap member 20 and the holder member 10 becomes sealed as a result of this turning of the cap member 20 the incursion of water or the like into the interior of the holder member 10 while the electric interdental cleaning brush 1 is being used can be prevented with certainty. Also, even when the electric interdental cleaning brush 1 is for example washed with the cap member 20 loose, as long as the cap member 20 is not so loose that the sealing effect of the seal ring 24 is lost, incursion of water or the like is prevented with certainty.

Also, because power to the electric motor 7 can be switched ON and OFF by bringing the cap side contact piece 35 into and out of contact with the holder side contact piece 33, the switch structure of the supply circuit can be simplified and the sealing structure thereof can be simplified, and the constitution of the device proper 5 can be greatly simplified.

Furthermore, the incursion of toothbrushing water and the like to between the meshing portions of the female thread portion 12 and the male thread portion 21 is prevented by the seal ring 24, and problems such as toothbrushing water hardening on the meshing portions of the thread portions 12 and 21 and making it difficult to turn the cap member 20 are prevented.

To reduce the frictional resistance between the cap member 20 and the holder member 10, the seal ring 24 may be made somewhat soft (hardness about 50) and its surface may be coated with a friction reducer such as teflon.

As shown in FIG. 8, a play G can be provided between the male thread portion 21 and the female thread portion 12 and the cap member 20 brought to a state wherein it is screwed in to a position such that the circuit supplying current to the electric motor 7 is just about to be closed; then by pushing the cap member 20 the cap side contact piece 35 can be moved through the play G between the male thread portion 21 and the female thread portion 12 and brought into contact with the holder side contact piece 33, thereby closing the supply circuit, and by ceasing pushing the cap member 20 the cap member 20 can be allowed to return to its original position under the spring force of the spring terminal 36 so that the cap side contact piece 35 moves away from the holder side contact piece 33 and the supply circuit is opened.

Next, a first other preferred embodiment consisting of the electric interdental cleaning brush 1 with partial modifications made thereto will be described. Parts of this preferred embodiment which are the same as parts in the preferred embodiment described above have been given the same reference numerals and a detailed description thereof will be omitted.

This electric interdental cleaning brush 40, as shown in FIG. 9, basically is so constituted that a female thread portion 61 formed in a cap member 60 is screwed into a male thread portion 51 formed on a holder member 50 and the cap member 60 is thereby fitted to the holder member 50.

The male thread portion 51 is formed on the right hand end portion of the holder member 50, a seal ring 52 is fitted in the vicinity of the base end of the male thread portion 51, and the right hand end portion of a holder side contact piece 53 is hooked around the right hand end portion of the female thread portion 51.

The cap member 60 is a bottomed cylindrical member; the male thread portion 61 which screws into the female thread portion 51 is formed on the inner wall of the left hand end vicinity of the cap member 60; a seal portion 63 having a seal surface 62 of greater internal diameter than the male thread portion 61 is formed on the left hand end portion of the cap member 60; a disclike cap side contact piece 64 is fixed to an inner back portion of the cap member 60 facing the holder side contact piece 53, and a spring terminal 65 consisting of a coil spring narrowing toward the left is fixed to the cap side contact piece 64.

In the electric interdental cleaning brush 40, the distance L1 between the center of the seal ring 52 and the right hand end of the holder side contact piece 53 is by design shorter than the distance L2 between the left hand end of the seal portion 63 and the left hand end surface of the cap side contact piece 64, and when the cap member 60 is screwed onto the holder member 50 and the seal ring 52 is first pressed upon by the left hand end of the seal portion 63, a clearance is formed between the holder side contact piece 53 and the cap side contact piece 64.

As in the preferred embodiment described earlier, in the electric interdental cleaning brush 40 also the electric motor 7 can be switched ON and OFF with the gap between the cap member 60 and the holder member 50 sealed by the seal ring 52, and there are the same actions and effects of the earlier preferred embodiment such as that water and the like can be effectively prevented from getting inside the holder member 50 while the electric interdental cleaning brush 40 is being used.

As shown in FIG. 10, a play G can be provided between the male thread portion 51 and the female thread portion 61 and the cap member 60 brought to a state wherein it is screwed in to a position such that the circuit supplying current to the electric motor 7 is just about to be closed; then by pushing the cap member 60 the cap side contact piece 64 can be moved through the play G between the male thread portion 51 and the female thread portion 61 and brought into contact with the holder side contact piece 53, thereby closing the supply circuit, and by ceasing pushing the cap member 60 the cap member 60 can be allowed to return to its original position under the spring force of the spring terminal 65 so that the cap side contact piece 64 moves away from the holder side contact piece 53 and the supply circuit is opened.

The operation of turning the cap member 20 or 60 may be given a sense of definiteness by forming long circumferential grooves in the holder member 10 or 50 or the cap member 20 or 60 and forming engaging projections on the cap member 20 or 60 or the holder member 10 or 50 which engage with the long grooves, restricting the range of turn of the cap member 20 or 60 by means of the engaging projections and the long grooves and thereby preventing the cap member 20 or 60 from being turned beyond the range of turn for switching the electric motor 7 ON and OFF.

In these preferred embodiments, the supply circuit is switched ON and OFF by the cap member 20 or 60 being turned; however, a separate switch may be provided in the supply circuit and the supply circuit may be switched ON and OFF by operation of this switch.

Next, a second other preferred embodiment consisting of the electric interdental cleaning brush 1 with partial modifications made thereto will be described. Parts of this preferred embodiment which are the same as parts in the preferred embodiments described above have been given the same reference numerals and a detailed description thereof will be omitted.

Figure 11:
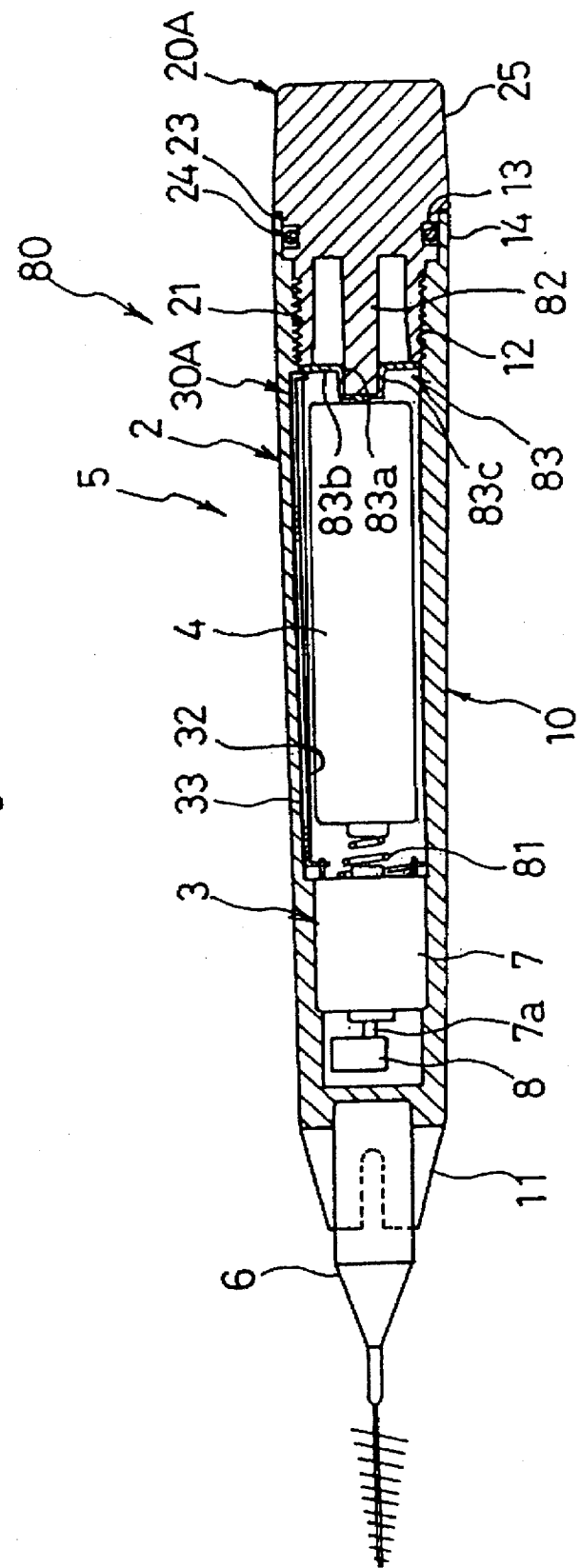
FIG. 11 is a view corresponding to FIG. 1 of an electric interdental cleaning brush according to a second other preferred embodiment.

This electric interdental cleaning brush 80 consists of the electric interdental cleaning brush 1 with the constitution of the wiring means 30 modified; as shown in FIG. 11 through FIG. 13, in the wiring means 30A used in this electric interdental cleaning brush 80, a spring terminal 81 contactable with the positive pole of the battery 4 is mounted on a substantially central portion of the right hand end of the electric motor 7; the base end portion of the spring terminal 81 is connected to one terminal of the electric motor 7, and the other contact of the electric motor 7 is connected to a bandlike holder side contact piece 33 as in the preferred embodiments described above.

A cap member 20A like the above-mentioned cap member 20 but without the slits 22 has formed on its inner back surface a pillarlike mounting portion 82 projecting to the left beyond the left hand end of the rest of the cap member 20A, and a cap side contact piece 83 is mounted on the end of the mounting portion 82.

The cap side contact piece 83 has an opening 83a through which the mounting portion 82 passes, and is fitted over the end portion of the mounting portion 82; the cap side contact piece 83 is integrally made up of an annular brim portion 83b extending from the vicinity of the mounting portion 82 to the left hand end portion of the cap member 20A and a bandlike contact portion 83c provided straddling the front side of the end of the mounting portion 82 and formed by so pressing the portion of the brim portion 83b corresponding to the opening 83a that it projects to the left; portions of the mounting portion 82 exposed at the sides of the contact portion 83c are melted to form a flat portion 82a, and the cap side contact piece 83 is held on the end of the mounting portion 82 by the flat portion 82a engaging with the brim portion 83b.

In the wiring means 30A, the right hand end of the spring terminal 81 makes contact with the positive pole of the battery 4, the battery 4 is urged to the right by the urging force of the spring terminal 81, and the negative pole of the battery 4 makes contact with the left end of the contact portion 83c. When the cap member 20A is screwed into the holder member 10 until it is inside the above-mentioned predetermined angle range, the right end of the holder side contact piece 33 makes contact with the outer circumferential edge portion of the left end surface of the brim portion 83b and current is supplied to the electric motor 7.

Thus, in the electric interdental cleaning brush 80, it is possible to fix the base end of the spring terminal 81 to one terminal of the electric motor 7 by hang-fixing or otherwise and the cap side contact piece 83 also can be easily mounted by forming the flat portion 82a by melting the portions of the mounting portion 82 which are exposed on either side of the contact portion 83c. Furthermore, the number of parts can be reduced, and because the constitution of the cap member 20A becomes simple the constitution of molds used to mold the cap member 20A can be greatly simplified.

The wiring means of the electric interdental cleaning brush 40 of the first other preferred embodiment may be constituted in the same way as in the second other preferred embodiment. That is, as shown in FIG. 14, a spring terminal 81 may be connected to one terminal of the electric motor 7, a pillarlike mounting portion 82 projecting to the left formed on the inner back surface of a cap member 60A, and a cap side contact piece 83 fitted to the left end of this mounting portion 82. As shown in FIG. 15, a cap member 60B like the cap member 60A but without the right hand half may be provided, a mounting portion 82 formed on the inner back surface of this cap member 60B, and a cap side contact piece 83 fixed with a brim portion 83b in contact with the inner back surface of the cap member 60B.

As shown in FIG. 16, engaging projections 84 may be formed projecting inward around the opening 83a of the brim portion 83b of the cap side contact piece 83, and when fitting the brim portion 83b to the mounting portion 82 the engaging projections 84 can be caused to engage with the circumferential surface of the mounting portion 82 and the cap side contact piece 83 thereby fixed to the cap member 20A, 60A or 60B. Also, as shown in FIG. 17, the contact portion 83c may be of cantilever form. Also, as shown in FIG. 18, the cap side contact piece 83 may be made hat-shaped with a brim, an annular projecting portion 83e may be provided projecting inward from a portion of the mounting portion 82 near the end thereof, an annular groove 82b which engages with the projecting portion 83e may be provided in the vicinity of the end of the mounting portion 82, and the cap side contact piece 83 may be fixed to the mounting portion 82 by the projecting portion 83e being caused to engage with the annular groove 82b. Instead of the flat portion 82a, without melting the portions of the mounting portion 82 exposed on either side of the contact portion 83c, the contact portion 83c may be fixed to the mounting portion 82 with an adhesive such as a hot melt.

Next, oral hygiene tools which can be removably attached to the holding portion 11 other than the interdental cleaning brush 6 will be described.

As one such oral hygiene tool, as shown in FIG. 19, a toothbrush 90 consisting of a bristle bed formed on the end of a shaft portion 6a and a plurality of bristles 90b embedded in this bristle bed 90a may be used.

As another such oral hygiene tool, as shown in FIG. 20, a nipple-type gum massager 91 consisting of a circular head portion 91a formed on the end of a shaft portion 6a and a tapered rubber member 91b mounted on this head portion 91a may be used.

As another such oral hygiene tool, as shown in FIG. 21, a gum massager 92 consisting of a baglike rubber member 92a mounted on the end of a shaft portion 6a and a plurality of protrusions 92b formed on the upper surface of this rubber member 92a may be used.

As still another oral hygiene tool, as shown in FIG. 22, a floss unit 93 consisting of a pair of arm portions 93a formed on the end of a shaft portion 6a and a length of dental floss 93b strung between the ends of the arm portions 93a may be used.

Next, the vibration state of the interdental cleaning brush 6 induced by the vibration generating means 3 will be described.

This vibration generating means 3 generates vibration by rotating the eccentric weight 8; as shown in FIG. 23, when the steel wire portion of the brush portion 6b is disposed coaxially with the center axis of the shaft portion 6a, as shown in FIG. 24 the end of the brush portion 6b rotates clockwise or counterclockwise in a circle of diameter (amplitude) R1. When the brush portion 6b and the shaft portion 6a are thus disposed coaxially, when the brush portion 6b is inserted between teeth and vibrated, mainly the interdental surrounding areas are cleaned. When with the brush portion 6b vibrating it is moved back and forth in the axial direction, the cleaning effect can be greatly increased.

As shown in FIG. 25, when the steel wire of the brush portion 6b is bent at its base portion through 90°, as shown in FIG. 26 the end of the brush portion 6b rotates clockwise or counterclockwise in a circle of diameter (amplitude) R2. When the brush portion 6b is bent like this, the brush portion 6b moves back and forth between the teeth and mainly cleans between the teeth.

In the vibration generating means 3, because vibration acts on the interdental cleaning brush 6 through the holder member 10, it is possible to adjust the amplitudes R1, R2 and the speed (the vibration frequency) of the end of the brush portion 6b by way of what part of the holder member 10 is held.

In other words, as shown in FIG. 27, because the confining action of the user's hand on the vibration of the tool becomes greater and the amplitude and frequency become smaller the nearer toward the tool end the holder member 10 is held, by holding the holder member 10 near its rear end when strong brushing is desired and holding the holder member 10 near its front end when gentle brushing is desired, it is possible to adjust the brushing strength.

INDUSTRIAL APPLICABILITY

In an oral hygiene instrument according to claim 1, by means of a simple construction wherein until the gap between the holder member and the cap member is sealed with certainty by the seal ring the holder side contact piece and the cap side contact piece are kept apart and the supply circuit is open, supplying of power to the vibration generating means when the cap member has become loose is prevented and the user is made known of the lack of sealing and the incursion of water and the like into the holder member is completely prevented. Also, the incursion of toothbrushing water and the like into where the holder side thread portion and the cap side thread portion mesh can be prevented with certainty, and problems caused by toothbrushing water hardening between the two meshing thread portions and making it difficult to turn the cap member can be prevented.

In an oral hygiene instrument according to claim 2, because switch contacts are constituted by the holder side contact piece and the cap side contact piece it is not necessary to separately provide a switch for opening and closing the supply circuit and furthermore it is possible to open and close the supply circuit with the gap between the holder member and the cap member sealed with certainty and the switch structure and the sealing structure thereof can be simplified and the constitution of the oral hygiene instrument can be greatly simplified. Also, when the supply circuit is closed, even if the instrument is washed with water, because watertightness is maintained, breakdowns and hardening making opening and closing of the thread portions difficult caused by the incursion of water do not occur. Furthermore, with the supply circuit open, even when the instrument is left between uses, frictional action of the sealing ring prevents the threads from loosening or tightening on their own.

In an oral hygiene instrument according to claim 3, because if the gap between the holder member and the cap member is not sealed properly it is impossible to close the supply circuit by operating the switch, the lack of sealing is made known to the user and the incursion of water and the like into the holder member is completely prevented.

In an oral hygiene instrument according to claim 4, by means of a simple constitution wherein an axial play is provided between the holder side thread portion and the cap side thread portion it is possible to close the supply circuit by pushing the cap member, and by having the holder side contact piece and the cap side contact piece double as the contacts of a push switch the switch structure and the sealing structure thereof can be simplified and the constitution of the oral hygiene instrument can be greatly simplified.

In an oral hygiene instrument according to claim 5, because the plurality of first and second slits are provided in the holding portion, the end of the holding portion can elastically expand and contract radially relatively greatly, and even if there are relatively large variations in the molding accuracy of the shaft portion the shaft portion can be held with certainty and the oral hygiene tool prevented from falling off, and because the first slits extend to the vicinity of the inner back surface of the holding portion, cleaning off of toothpaste powder and the like clogging the inner back portion of the holding portion is easy. Also, because the shaft portion of the oral hygiene tool can be of a simple bar shape, manufacturing of the oral hygiene instrument can be simplified.

In an oral hygiene instrument according to claim 6, by providing a simple engaging projection on the inner circumferential side of the holding portion in the vicinity of the end thereof, axial movement of the oral hygiene tool is restricted and it is more effectively prevented from coming off.

In an oral hygiene instrument according to claim 7, by providing simple tongue projections or protrusions on the outer circumferential surface of the oral hygiene tool, rotation of the oral hygiene tool about the shaft portion is restricted and the operability of the oral hygiene instrument is greatly increased.

In an oral hygiene instrument according to claim 8, because a spring terminal is fitted to the vibration generating means and a cap side contact piece comprising a brim portion and a contact portion is fitted to the cap member, the constitution of the cap member can be greatly simplified and compared to a case wherein a spring terminal is fixed to the cap member the work of installing the spring terminal can be greatly simplified.

In an oral hygiene instrument according to claim 9, the cap side contact piece can easily be fitted to the cap member by the cap side contact piece being press-fitted onto the mounting portion and the engaging projection being caused to engage with the outer circumferential surface of the mounting portion.

In an oral hygiene instrument according to claim 10, because with the cap side contact piece fitted to the mounting portion a flat portion is formed by melting the portions of the mounting portion exposed on either side of the contact portion, it is possible to easily fix the cap side contact piece to the cap member by preventing the cap side contact piece from falling by means of the flat portion.

In an oral hygiene instrument according to claim 11, as in claim 1, because until the gap between the holder member and the cap member is sealed with certainty by the seal ring the supply circuit cannot be closed and the vibration generating means cannot be driven, as a result it is made known to the user that sealing is not being effected properly and the incursion of toothbrushing water or the like into where the holder member and the cap member mesh is prevented with certainty by the seal ring. Also, as in the instrument of claim 5, because a plurality of first slits and second slits are provided in the holding portion, the end of the holding portion can elastically expand and contract radially relatively greatly, and even if there are relatively large variations in the molding accuracy of the shaft portion the shaft portion can be held with certainty and the oral hygiene tool prevented from falling off, and because the first slits extend to the vicinity of the inner back surface of the holding portion, cleaning off of toothpaste powder and the like clogging the inner back portion of the holding portion is easy. Also, as in the instrument of claim 8, because the spring terminal is fitted to the vibration generating means and the cap side contact piece comprising the brim portion and the contact portion is fitted to the cap member, the constitution of the cap member can be greatly simplified and compared to a case wherein a spring terminal is fixed to the cap member the work of installing the spring terminal can be greatly simplified.

What is claimed is:

1. An oral hygiene instrument comprising:

a holder member capable of accommodating a battery and provided with a holder side thread portion at a first end thereof and watertightly closed at a second end thereof;

an oral hygiene tool removably attached to said second end of said holder member and comprising any one of a group consisting of a toothbrush, an interdental cleaning brush, a gum massaging tool and a nipple-type gum massaging tool, mounted on an end of a shaft portion thereof;

vibration generating means, housed in said second end of said holder member, for vibrating said oral hygiene tool by way of said holder member;

a cap member having a cap side thread portion for meshing with said holder side thread portion, said cap member being removably attached to said first end of said holder member and closing an opening in said first end of said holder member;

a seal ring fitted on a portion of any one of said holder member and said cap member at an external end of a part where said holder member meshes with said cap member, said seal ring being pressed upon by any one of said cap member and said holder member and seals a gap between said holder member and said cap member within a range of a predetermined angle of screwing of said cap member with respect to said holder member from a late stage to completion of said screwing; and a holder side contact piece and a cap side contact piece mounted in said holder member and said cap member, respectively, which approach each other when said cap member is screwed with respect to said holder member and in said range of said predetermined angle make contact and close a circuit supplying electricity to said vibration generating means.

2. The oral hygiene instrument according to claim 1, wherein said holder side contact piece and said cap side contact piece constitute a switch of said circuit supplying electricity to said vibration generating means, and said circuit supplying electricity to said vibration generating means is opened and closed by said cap member being turned in said range of said predetermined angle.

3. The oral hygiene instrument according to claim 1, wherein a switch means for opening and closing said circuit supplying electricity to said vibration generating means is provided in any one of said holder member and said cap member.

4. The oral hygiene instrument according to claim 1, wherein an axial play is provided between said holder side thread portion and said cap side thread portion;

a spring terminal, which is pressed upon by one electric pole of said battery, is provided; and an urging force of said spring terminal which urges said cap member away from said holder member.

5. An oral hygiene instrument comprising:

a holder member capable of accommodating a battery, said holder member having a first end and a second end;

a cap member capable of watertightly closing a first end of said holder member;

an oral hygiene tool comprising any one of a group consisting of a toothbrush, an interdental cleaning brush, a gum massaging tool and a nipple-type gum massaging tool, mounted on a first end of a shaft portion thereof;

a bottomed cylindrical holding part watertightly closing said second end of said holder member and capable of holding therein a second end of said shaft portion of said oral hygiene tool and provided with a plurality of first slits extending from said end to a vicinity of an inner back surface of said holding part and a plurality of second slits shorter that said first slits extending from said end toward said inner back surface of said holding part; and vibration generating means, housed in said second end of said holder member, for vibrating said oral hygiene tool by way of said holder member.

6. The oral hygiene instrument according to claim 5, wherein an engaging projection for restricting axial movement of said shaft portion of said oral hygiene tool is provided on an inner circumferential side of a portion of said holding part near said end thereof.

7. The oral hygiene instrument according to any one of claim 5 and claim 6, wherein any one of a protrusion and an axial tongue projection for engaging with any one of said first slits and said second slits is provided on an outer circumferential surface of said shaft portion of said oral hygiene tool.

8. An oral hygiene instrument comprising:

a holder member capable of accommodating a battery and having a first end which is open and a second end which is watertightly closed;

a bottomed cylindrical cap member capable of watertightly closing an opening in said first end of said holder member and having a projecting mounting portion provided in a central portion of an inner back surface of said cap member;

an oral hygiene tool removably attached to said second end of said holder member and comprising any one of a group consisting of a toothbrush, an interdental cleaning brush, a gum massaging tool and a nipple-type gum massaging tool, mounted on a first end of a shaft portion thereof;

vibration generating means, housed in said second end of said holder member, for vibrating said oral hygiene tool by way of said holder member;

a holder side contact piece extending axially along an inner wall surface of said holder member and having a first end disposed in a vicinity of said first end of said holder member and a second end electrically connected to said vibration generating means;

a cap side contact piece mounted on a mounting portion and having an annular brim portion fitting around said mounting portion and capable of making sliding contact with said holder side contact piece and a contact portion extending from said brim portion to a front side of an end of said mounting portion;

a spring terminal having a first end electrically connected to said vibration generating means and a second end disposed contactably with a first electric pole of a battery accommodated in said holder member, wherein when said cap member is fitted to said holder member said second end of said spring terminal is pressed against said first electric pole of said battery and causes a second electric pole of said battery to press against said contact portion of said cap side contact piece.

9. The oral hygiene instrument according to claim 8, wherein an engaging projection which engages with said mounting portion is provided projecting inwardly at an opening portion in said brim portion through which said mounting portion passes.

10. The oral hygiene instrument according to claim 8, wherein said contact portion straddles said end of said mounting portion and said cap side contact piece is fixed to said cap member by a flat portion formed by melting portions of said mounting portion exposed on any one of sides of said contact portion.

11. An oral hygiene instrument comprising:

a holder member provided at a first end thereof with a holder side thread portion and capable of accommodating a battery;

a bottomed cylindrical cap member fitted to said first end of said holder member and closing an opening in said first end of said holder member and provided at an end thereof with a cap side thread portion for mating with said holder side thread portion and having a mounting portion projecting from a central portion of an inner back surface thereof;

an oral hygiene tool comprising any one of a group consisting of a toothbrush, an interdental cleaning brush, a gum massaging tool and a nipple-type gum massaging tool, mounted on a first end of a shaft portion thereof;

a bottomed cylindrical holding part watertightly closing a second end of said holder member and capable of holding therein a second end of said shaft portion of said oral hygiene tool and provided with a plurality of first slits extending from said end to a vicinity of an inner back surface of said holding part and a plurality of second slits shorter that said first slits extending from said end toward said inner back surface of said holding part;

vibration generating means, housed in said second end of said holder member, for vibrating said oral hygiene tool by way of said holder member;

a seal ring fitted on a portion of any one of said holder member and said cap member at an external end of a part where said holder member meshes with said cap member, said seal ring being pressed upon by any one of said cap member and said holder member and seals a gap between said holder member and said cap member within a range of a predetermined angle of screwing of said cap member with respect to said holder member from a late stage to completion of said screwing;

a holder side contact piece extending axially along an inner wall surface of said holder member and having a first end disposed in a vicinity of said first end of said holder member and a second end electrically connected to said vibration generating means;

a cap side contact piece mounted on a mounting portion and having an annular brim portion fitting around said mounting portion and a contact portion extending from said brim portion to a front side of an end of said mounting portion, said cap member being screwed with respect to said holder member causing said brim portion to approach said holder side contact piece and in said range of said predetermined angle, make contact with said holder side contact piece and close a circuit supplying electricity to said vibration generating means; and a spring terminal having a first end electrically connected to said vibration generating means and a second end disposed contactably with a first electric pole of a battery accommodated in said holder member, wherein when said cap member is fitted to said holder member said second end of said spring terminal is pressed against said first electric pole of said battery and causes a second electric pole of said battery to press against said contact portion of said cap side contact piece.

* * * * *